United States Patent [19]

Neefe

[11] 3,984,485

[45] Oct. 5, 1976

[54] WETTABLE POLYMERIC MATERIALS PREPARED FROM 2-50% BY WT. N-(1,1-DIMETHYL-3-OXOBUTYL)ACRYLAMIDE, 2.5% BY WT. CROSSLINKING AGENT AND METHYL METHACRYLATE

[76] Inventor: Charles W. Neefe, P.O. Drawer 429, Big Spring, Tex. 79720

[22] Filed: June 6, 1975

[21] Appl. No.: 584,283

Related U.S. Application Data

[63] Continuation-in-part of Ser. No. 404,352, Oct. 9, 1973, which is a continuation-in-part of Ser. No. 45,333, June 11, 1970, which is a continuation-in-part of Ser. No. 562,022, May 16, 1966, abandoned.

[52] U.S. Cl. ............................................ 260/63 UY
[51] Int. Cl.² .................... C08G 2/00; C08G 4/00; C08F 120/70; C08F 220/58
[58] Field of Search ..................... 260/80.73, 63 UY

[56] References Cited
UNITED STATES PATENTS

| | | | |
|---|---|---|---|
| 3,277,056 | 10/1966 | Coleman | 260/63 UY |
| 3,425,942 | 2/1969 | Goleman | 260/80.3 |
| 3,497,467 | 2/1970 | Coleman | 260/63 UY |
| 3,518,326 | 6/1970 | Forsberg | 260/64 |
| 3,660,545 | 5/1972 | Wichterle | 260/80.73 |
| 3,663,490 | 5/1972 | Sarem | 260/80.73 |
| 3,699,089 | 10/1972 | Wichterle | 260/80.73 |

*Primary Examiner*—Joseph L. Schofer
*Assistant Examiner*—Herbert J. Lilling

[57] ABSTRACT

A copolymer of polymethyl methacrylate and N-(1,1-dimethyl-3-oxobutyl) acrylamide having a wettable surface and low water absorption and low gas transmission.

3 Claims, No Drawings

WETTABLE POLYMERIC MATERIALS PREPARED FROM 2-50% BY WT. N-(1,1-DIMETHYL-3-OXOBUTYL)ACRYLAMIDE, 2.5% BY WT. CROSSLINKING AGENT AND METHYL METHACRYLATE

RELATED APPLICATIONS

This is a continuation-in-part of application Ser. No. 404,352, filed Oct. 9, 1973 entitled DRUG DELIVERY METHOD now pending, which is a continuation-in-part of Pat. No. 3,786,812, filed Mar. 10, 1972 entitled CONTACT LENS FOR OCULAR DRUG DELIVERY which is a continuation-in-part of Ser. No. 45,333, filed June 11, 1970, which is a continuation-in-part of Ser. No. 562,022, filed May 16, 1966 now abandoned.

THE PRIOR ART

Ridged or hard contact lenses have been made from polymethyl methacrylate. This material is hydrophobic and has a contact angle of 60° to 64°. This high contact angle results in the need for a wetting agent to lower the contact angle to 30° to 40° and the water to form a smooth layer on the lens. Comfort and wearability are greatly improved by the use of wetting solutions. The use of such solutions has become universal in the hard contact lens industry. The contact lens industry could not have developed without wetting solutions to improve comfort. This hydrophobic material has been used because it was the only material available having the required dimensional stability and compatibility with ocular tissue. Soft lenses are considered a different industry as the optical properties are different due to the soft lens assuming the shape of the cornea and therefore not correcting astigmatism and other disorders such as kertaconus.

DISCLOSURE

The present invention provides a modified methyl methacrylate having a contact angle of 20° when dry and 10° when hydrated. This is accomplished by adding from 2 percent to 50 percent by weight the monomer N-(1,1 dimethyl-3-oxobutyl) acrylamide to the monomer methyl methacrylate and polymerizing to form a copolymer. A cross-linking agent must be added to preserve the dimensional stability of the material. The water absorption is increased by adding the N-(1,1 dimethyl-3-oxobutyl) acrylamide with corresponding loss of dimensional stability. A crosslinking agent such as allyl dimethacrylate or ethylene dimethacrylate is added to provide a low water absorption of 2.5% by weight and maintain the required dimensional stability and good wetability.

The polymerization is carried out using any of the standard processes used with methyl methacrylate and well known to the art. Catalysts such as azobis (2 methylpropionitrile), teriary-butylperoctoate or benzol peroxide may be used. The material may be cast in silicone molds to form contact lens blanks or cast in rods which are cut into discs.

DESCRIPTION OF THE PREFERRED EMBODIMENT

A typical formulation is as follows. In a glass tube place 2.5g ethylene dimethacrylate, 5g N-(1,1 dimethyl-3-oxobutyl) acrylamide added to 92.5g methyl methacrylate, and a catalyst of 0.07g azobis (2 methyl propionitrile) purge of oxygen and place under a nitrogen blanket and heat to 40°C for 12 hours to polymerize. The solid copolymer is post cured at 70°C for 16 hours. Contact lenses are made from the material and have a contact angle of less than 20° when hydrated. The lenses are stored in a solution of 0.9% sodium chloride, 0.001% thimerosal, 0.1% ethylenediaminetetraacetic acid.

What is claimed is:

1. A material for the manufacture of contact lenses having a water absorption of 2.5% by weight and a water contact angle of less than 20° when hydrated comprising 2.5% by weight ethylene dimethacrylate, 5% by weight N-(1,1 dimethyl-3-oxobutyl) acrylamide, and 92.5% by weight methyl methacrylate.

2. A material as in claim 1 comprising 2.5% by weight allyl methacrylate, 5% by weight N-(1,1 dimethyl-3-oxobutyl) acrylamide, and 92.5% by weight methyl methacrylate.

3. A material for the manufacture of contact lenses having a water absorption of 2.5% by weight and a water contact angle of less than 20° when hydrated comprising 2.5% by weight of a crosslinking agent selected from ethylene dimethacrylate or allyl methacrylate, 2% to 50% by weight N-(1,1 dimethyl-3-oxobutyl) acrylamide and the remainder methyl methacrylate.

* * * * *